US008870757B2

(12) United States Patent
Angelopoulou et al.

(10) Patent No.: US 8,870,757 B2
(45) Date of Patent: Oct. 28, 2014

(54) METHOD, DEVICE AND ENDOSCOPY CAPSULE TO DETECT INFORMATION ABOUT THE THREE-DIMENSIONAL STRUCTURE OF THE INNER SURFACE OF A BODY CAVITY

(75) Inventors: Elli Angelopoulou, Nürnberg (DE); Aleksandar Juloski, Nuremberg (DE); Rainer Kuth, Höchstadt (DE); Philip Mewes, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 227 days.

(21) Appl. No.: 13/582,669

(22) PCT Filed: Feb. 24, 2011

(86) PCT No.: PCT/EP2011/052748
§ 371 (c)(1),
(2), (4) Date: Nov. 19, 2012

(87) PCT Pub. No.: WO2011/107392
PCT Pub. Date: Sep. 9, 2011

(65) Prior Publication Data
US 2013/0060085 A1 Mar. 7, 2013

(30) Foreign Application Priority Data

Mar. 2, 2010 (DE) .......................... 10 2010 009 905

(51) Int. Cl.
*A61B 1/06* (2006.01)
*A61B 1/04* (2006.01)
*A61B 6/00* (2006.01)
*A61B 1/00* (2006.01)

(52) U.S. Cl.
CPC ............. *A61B 1/041* (2013.01); *A61B 1/00158* (2013.01); *A61B 1/0638* (2013.01); *A61B 1/00193* (2013.01); *G06T 2210/41* (2013.01); *A61B 1/00179* (2013.01)
USPC ............................ 600/160; 600/109; 600/476

(58) Field of Classification Search
CPC .... A61B 1/041; A61B 19/52; A61B 19/5212; A61B 1/00009
USPC .................. 600/160, 109, 476, 477; 382/128; 348/46; 356/601–603
See application file for complete search history.

(56) References Cited

U.S. PATENT DOCUMENTS 6,028,606 A  2/2000 Kolb et al.
6,097,394 A  8/2000 Levoy et al.
(Continued)

FOREIGN PATENT DOCUMENTS

DE  10 2005 032 579      7/2006
DE  10 2005 032 140 A1   1/2007
(Continued)

OTHER PUBLICATIONS

The Study for Automatic 3D Reconstruction of Endoscopic Video Image, Nagakura et al. IEEE (2007).
(Continued)

*Primary Examiner* — John P Leubecker
*Assistant Examiner* — Ronald D Colque
(74) *Attorney, Agent, or Firm* — Schiff Hardin LLP

(57) ABSTRACT

In a method and a device to detect information about the three-dimensional structure of the inner surface of a body cavity of a patient with an endoscopy capsule introduced into said body cavity, a first partial region of the inner surface of the body cavity is illuminated with at least one light source arranged in the endoscopy capsule and an image of a second partial region that is illuminated by the first partial region and differs from the first partial region. The three-dimensional structure of the second partial region is known, and the second partial region is acquired with at least one camera arranged in the endoscopy capsule. Information about the three-dimensional structure of the first partial region is derived using the intensity values in this image.

7 Claims, 1 Drawing Sheet

(56) References Cited

U.S. PATENT DOCUMENTS

| | | |
|---|---|---|
| 7,343,036 B2 | 3/2008 | Kleen et al. |
| 2002/0198439 A1* | 12/2002 | Mizuno .................. 600/109 |
| 2003/0060702 A1 | 3/2003 | Kuth et al. |
| 2004/0264754 A1 | 12/2004 | Kleen et al. |
| 2005/0043583 A1 | 2/2005 | Killmann et al. |
| 2005/0049462 A1 | 3/2005 | Kanazawa |
| 2005/0124858 A1 | 6/2005 | Matsuzawa et al. |
| 2005/0171398 A1* | 8/2005 | Khait et al. ............. 600/102 |
| 2006/0209185 A1 | 9/2006 | Yokoi |
| 2006/0217593 A1 | 9/2006 | Gilad et al. |
| 2009/0062613 A1 | 3/2009 | Mitsuhashi |
| 2009/0306474 A1* | 12/2009 | Wilson .................. 600/109 |
| 2011/0304717 A1 | 12/2011 | Degenhardt et al. |

FOREIGN PATENT DOCUMENTS

| | | |
|---|---|---|
| DE | 10 2007 030 747 A1 | 10/2008 |
| JP | 1-209417 A | 8/1989 |

OTHER PUBLICATIONS

"Robust Motion Estimation and Structure Recovery from Endoscopic Image Sequences With an Adaptive Scale Kernel Consensus Estimator," Wang et al., IEEE CVPR 2008, pp. 1-7.

* cited by examiner

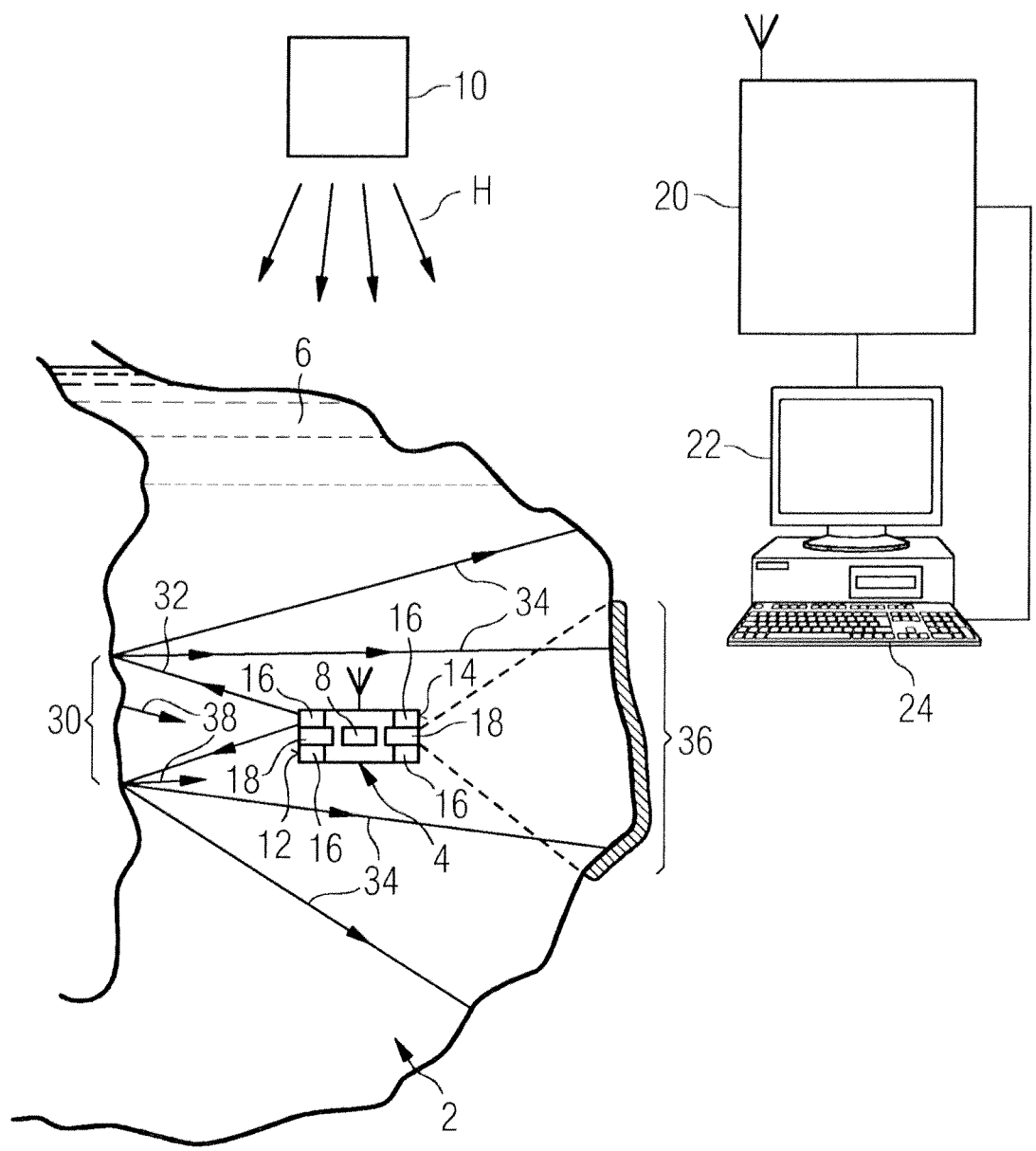

METHOD, DEVICE AND ENDOSCOPY CAPSULE TO DETECT INFORMATION ABOUT THE THREE-DIMENSIONAL STRUCTURE OF THE INNER SURFACE OF A BODY CAVITY

BACKGROUND OF THE INVENTION

1. Field of the Invention

The invention concerns a method and a device to detect information about the three-dimensional structure of a body cavity of a patient with an endoscopy capsule introduced into said body cavity. The invention also concerns an endoscopy capsule suitable for implementation of the method.

2. Description of the Prior Art

For optical examination of the inner surface of a body cavity (for example the gastrointestinal tract of a patient) it is basically known to introduce rigid or flexible endoscopes via body orifices, which endoscopes are mechanically controlled by the hand of the surgeon and enable a direct observation of the body cavity.

As an alternative to such manually controlled endoscopes, for example, from US 2006/0 209 185 A1, US 2005/0 124 858 A1 and DE 101 42 253 C1 it is known to introduce an endoscopy capsule into the body cavity, which endoscopy capsule acquires—with a video camera arranged on the front side of said endoscopy capsule—an image of the inner surface of the body cavity that is located in the field of view of the video camera without a fixed connection to the outside of the body cavity. The endoscopy capsule known from DE 101 42 253 C1 can, moreover, be freely maneuvered in the body cavity.

The spatial perception is severely limited by the monocular optics used in the known endoscopy capsule, and is based only on experimental values and the surgeon interprets brightness and color tone in the video image based on his or her anatomical knowledge and derives spatial information from these characteristics.

However, a 3D reconstruction of the body cavity is desirable both from a diagnostic standpoint and to control an endoscopy capsule that can be freely maneuvered in the body cavity.

In principle, a stereoscopic viewing would be possible if two video cameras could be used in the endoscopy capsule. Although an endoscopy device in which the endoscopy capsule includes two video cameras is known from DE 103 23 216 B3, these are arranged at opposite facing ends of the endoscopy capsule. Even in this known endoscopy capsule, in spite of the presence of two video cameras, a binocular viewing is not possible since their fields of view do not overlap in a manner that allows a stereoscopic view to be produced.

However, a stereoscopic image generation with two video cameras that are spaced apart from one another and whose image fields overlap is possible only to a limited extent due to the small structural dimensions of an endoscopy capsule.

SUMMARY OF THE INVENTION

An object of the present invention is to provide a method to detect information about the three-dimensional structure of the inner surface of a body cavity of a patient that can be implemented even given limited structural relationships with an endoscopy capsule introduced into the body cavity. A further object of the invention is to provide a device to implement such a method.

This object is achieved according to the invention by a method wherein a first partial region of the inner surface of the body cavity is illuminated with at least one light source arranged in the endoscopy capsule. An image of a second partial region that is illuminated by the first partial region and differs from said first partial region, the three-dimensional structure of which second partial region is known, is acquired with at least one camera arranged in the endoscopy capsule. Using the intensity values in this image, information about the three-dimensional structure of the first partial region is now derived.

By evaluating the image information of the indirectly illuminated second partial region, it is possible to obtain structure information of partial regions of the inner surface of the body cavity that are located outside of the image field of the camera. Both making the diagnosis and for endoscopy capsules that are freely maneuverable in the body cavity the navigation thereof, are facilitated by a 3D reconstruction (possible in this way) of the area illuminated by the light source.

Given the use of endoscopy capsules that are freely maneuverable in the body cavity, these can be controlled in optimal positions and directions from which it is possible to generate images that can be optimally assessed for diagnostic purposes.

If the first and second partial region are opposite one another, a reconstruction of the three-dimensional structure that forms the surfaces of the first partial region is particularly facilitated since, due to the diffuse reflection of the light striking the first partial region, the inner surface opposite this is illuminated with maximum intensity.

Moreover, if the first partial region is illuminated with a temporal succession of light pulses of different spectral composition, and if an image of the second partial region is respectively acquired and evaluated at each light pulse, additional conclusions about the frequency dependency of the degree of reflection of the first partial region can be derived.

An endoscopy capsule suitable to implement the method includes a number of light sources and at least one camera whose field of view lies outside of the spatial area illuminated by the light sources. In a preferred embodiment, the endoscopy capsule moreover includes a magnet device with which it is possible to magnetically maneuver the endoscopy capsule via application of an external magnetic field.

BRIEF DESCRIPTION OF THE DRAWINGS

The single FIGURE schematically illustrates a device according to the invention.

DESCRIPTION OF THE PREFERRED EMBODIMENTS

As shown in the figure the device has an endoscopy capsule 4 that is introduced into a body cavity 2 (the stomach, for example) of a patient. The endoscopy capsule 4 can be freely maneuvered within the body cavity 2 filled with a fluid. For this purpose the endoscopy capsule 4 has a bar magnet 8 (indicated only schematically in the figure). The control of the movement and alignment of the endoscopy capsule 4 takes place without contact via a magnetic field H that is generated by a magnet system arranged outside of the patient.

On respective opposite facing sides 12 and 14 of the endoscopy capsule 4 are a camera 18 and a number of light sources 16, of which two are illustrated schematically in the figure. The light emitted by the light sources 16 respectively arranged on one side of the capsule 4 differs with regard to spectral composition. Three light sources 16 are advantageously provided that respectively emit red, green and blue light. The images acquired by the cameras 18 are transmitted via radio to an external evaluation device 20, and are processed therein and supplied to a monitor 22 after reconstruction of the three-dimensional structure of the inner surface of the body cavity 2.

Moreover, an input device 24 in the form of a keyboard is illustrated in the figure, with which input device 24 it is possible to generate control commands with which the light sources 16 and cameras 18 of the endoscopy capsule 4 as well as the movements of the endoscopy capsule 4 are controlled.

In the figure the situation is shown in which one of the light sources 16 arranged on the facing side 12 emits light (for example a light pulse) and in this way illuminates a first partial region 30 of the inner surface of the body cavity 2. The light bundle 32 emitted by the light source 16 is diffusely reflected by the first partial region 30, and the light 34 reflected in all directions in this manner strikes the inner surface of the body cavity 2 that is opposite the partial region 30, such that this is indirectly illuminated.

A second partial region 36 that is located in the image field (illustrated with dashed lines) of the camera 18—which second partial region 36 is located within the indirectly illuminated inner surface—is now acquired with said camera 18, which is arranged on the opposite facing side 14 of the endoscopy capsule 4.

The invention proceeds from the insight that the intensity of the light reflected by the first partial region 30 takes place perpendicular to the surface, i.e. parallel to the respective surface normal 38. The intensity distribution of the image of the second partial region 36 that is acquired by the opposite camera 18 therefore allows information about the spatial structure of the first partial region 30 since the intensity of the light striking the second partial region 36 changes depending on the distance.

A three-dimensional reconstruction of the structure of the first partial region 30 is possible if the three-dimensional structure of the second partial region has been determined with known structure-acquiring methods. For example, this structure determination can be implemented with a method designated as "structure from motion", in which the endoscopy capsule 4 is directed over the surface at a clearance and successive images are acquired. By associating image points of successively acquired images with one and the same subject point, the respective distance between camera and subject point can be calculated via triangulation, and the structure of the surface of the subject can therefore be reconstructed.

In the exemplary embodiment, multiple light sources 16 that differ with regard to their spectral composition are arranged on each side. If these are activated in temporal succession, information about the spectral albedo values of the first partial region 30 can additionally be determined if the local spectral albedo values of the second partial region 36 are correspondingly known.

Although modifications and changes may be suggested by those skilled in the art, it is the intention of the inventors to embody within the patent warranted heron all changes and modifications as reasonably and properly come within the scope of their contribution to the art.

We claim as our invention:

1. A method to detect information representing a three-dimensional structure of an inner surface of a body cavity of a patient, comprising:
   introducing an endoscopy capsule into a body cavity of a patient, said body cavity having an inner surface;
   with a light source in said introduced endoscopy capsule, illuminating a first portion of said inner surface of said body cavity;
   with a camera in the endoscopy capsule, acquiring an image of a second portion of said inner surface of said body cavity that differs from said first portion and is illuminated by said first portion, said second portion having a three-dimensional structure that is known; and
   supplying said image from said endoscopy capsule to a processor and, in said processor, automatically deriving information representing a three-dimensional structure of said first portion of said inner surface from intensity values in said image.

2. A method as claimed in claim 1 comprising employing an endoscopy capsule that is freely maneuverable in said body cavity.

3. A method as claimed in claim 1 wherein said first portion of said inner surface and said second portion of said inner surface are opposite each other in said body cavity.

4. A method as claimed in claim 1 comprising illuminating said first portion of said inner surface in temporal succession with light pulses of respectively different spectral compositions, and acquiring respective images of said second portion of said inner surface after each light pulse, and evaluating the respective images for each light pulse.

5. A device for detecting information representing a three-dimensional structure of an inner surface of a body cavity of a patient, comprising:
   an endoscopy capsule configured for introduction into a body cavity of a patient, said body cavity having an inner surface;
   said endoscopy capsule comprising a light source that illuminates a spatial area of said inner surface, and a camera having an imaging field of view that is outside of said spatial area; and
   a control unit configured to operate said light source and said camera to cause said light source to illuminate said spatial area and to acquire an image of another area, outside of said spatial area, of said inner surface of said body cavity that is illuminated by illumination of said spatial area, and to evaluate said image to derive information representing a three-dimensional structure of said area outside of said spatial area from intensity values in said image.

6. A device as claimed in claim 5 wherein said endoscopy capsule is configured for free maneuverability in said body cavity.

7. A device as claimed in claim 5 wherein said endoscopy capsule comprises a plurality of light sources operated by said control unit to respectively emit light of different spectral compositions.

* * * * *